United States Patent
Zhu (10) Patent No.: US 9,889,296 B2
(45) Date of Patent: Feb. 13, 2018

(54) SIGNAL ADJUSTMENT FOR ELECTROTHERAPY

(71) Applicant: TrioWave Technologies, San Jose, CA (US)

(72) Inventor: Huiyou Zhu, Fremont, CA (US)

(73) Assignee: TRIOWAVE TECHNOLOGIES, INC., Fremont, CA (US)

(*) Notice: Subject to any disclaimer, the term of this patent is extended or adjusted under 35 U.S.C. 154(b) by 24 days.

(21) Appl. No.: 14/823,990

(22) Filed: Aug. 11, 2015

(65) Prior Publication Data

US 2016/0059008 A1    Mar. 3, 2016

Related U.S. Application Data

(60) Provisional application No. 62/043,894, filed on Aug. 29, 2014.

(51) Int. Cl.
*A61N 1/32* (2006.01)
*A61N 1/36* (2006.01)
*A61N 1/04* (2006.01)

(52) U.S. Cl.
CPC ......... *A61N 1/326* (2013.01); *A61N 1/36014* (2013.01); *A61N 1/0468* (2013.01)

(58) Field of Classification Search
CPC ............... A61N 1/326; A61N 1/36021; A61N 1/36046; A61N 1/32
USPC ........................................................ 607/50
See application file for complete search history.

(56) References Cited

U.S. PATENT DOCUMENTS

| | | | |
|---|---|---|---|
| 4,105,023 A | 8/1978 | Marchese | |
| 6,035,236 A | 3/2000 | Jarding et al. | |
| 6,275,735 B1 | 8/2001 | Jarding | |
| 6,535,767 B1 | 3/2003 | Kronberg | |
| 7,909,861 B2 | 3/2011 | Balachandran et al. | |
| 9,220,894 B1 * | 12/2015 | Zhu | A61N 1/326 |
| 2016/0059020 A1 * | 3/2016 | Zhu | H01M 10/425 |
| | | | 607/50 |

* cited by examiner

*Primary Examiner* — Carl H Layno
*Assistant Examiner* — Jon Eric C Morales
(74) *Attorney, Agent, or Firm* — Sheppard Mullin Richter & Hampton LLP (57) ABSTRACT

Battery-driven stimulators for electrotherapy usually equip with a small battery to generate specified current waveforms applied to human body for stimulation. Such current waveforms can easily get into a saturated status due to high bio-impedance and low battery power. The present disclosure provides a system in which the waveform is adjusted according to feedbacks taken from a patient to reduce or avoid saturation.

10 Claims, 5 Drawing Sheets

SIGNAL ADJUSTMENT FOR ELECTROTHERAPY

CROSS-REFERENCE TO RELATED PATENT APPLICATIONS

This application claims the benefit under 35 U.S.C. § 119(e) of U.S. Provisional Application 62/043,894, filed Aug. 29, 2014, which is incorporated herein by reference in its entireties and for all purposes.

BACKGROUND

Electrotherapy is the practice of using electronic stimulation to help the body heal and recover after it has been damaged. With electrotherapy, a patient can control pain and speed up the healing process.

A common form of electrotherapy is transcutaneous electrical nerve stimulation (TENS). TENS uses small electrodes that can be fastened to the skin. The therapist administering the treatment can then adjust the amount of electricity that flows through the electrodes by a dial on the TENS device. This allows one to adjust the level of electricity to the comfort level and treatment level needed by the patient.

Electrotherapy works to heal in two main ways, reducing swelling and increasing circulation to the affected area. The reduced swelling allows more blood to rush to the areas that need healing. This also increases the circulation of the affected area. The increased blood flow allows oxygen and nutrients as well as healer cells of the body to start working on repairing the damaged tissue.

Electrotherapy works in pain management in two ways. Inside the body are large amounts of nerve cells and nerve pathways. These allow the brain to send signals to the body and the body to send signals to the brain. One of these signals is pain. Electrotherapy works by interrupting the signal for pain, keeping the patient from feeling it. Electrotherapy also activates the body to produce endorphins. Endorphins are chemicals that act as the body's natural pain killers.

SUMMARY

The present disclosure, in one embodiment, provides a micro current therapy device comprising a pulse wave generator configured to generate a pulse waveform signal; a first electrode and a second electrode each in electric communication with the pulse wave generator; an analog-to-digital converter (ADC) in electric communication with the first electrode and the second electrode and configured to measure a voltage between the first electrode and the second electrode when the first electrode and the second electrode are connected to a conductive subject at two separate locations; and a controller comprising a processor, a memory and program code which, when executed by the processor, configures the controller to: (a) receive the voltage from the ADC as input at a predetermined schedule; and (b) increase the amplitude by a predetermined increase interval if the voltage is lower than a voltage upper limit, or lower the amplitude to a base amplitude level if the voltage is the same as or higher than voltage threshold.

In some aspects, the schedule has a predetermined interval. In some aspects, the interval is from 10 seconds to 60 seconds.

In some aspects, the voltage upper limit is from 3000 mV to 9000 mV. In some aspects, the base amplitude level is from 0.01 mA to 60 mA. In some aspects, the increase interval is from 0.005 mA to 2 mA. In some aspects, the pulse waveform has a frequency from 0.1 Hz to 200 Hz. In some aspects, the pulse waveform has an amplitude from 1 µA to 200 µA.

Also provided, in one embodiment, is a method for improving healing of a human subject in need thereof, comprising connecting the first electrode and the second electrode of the device of the present disclosure to two locations of the human subject to the subject and configuring the device to apply wave forms to the human subject, thereby improving healing of the human subject. In some aspects, the device further comprises a user interface allowing a user to adjust the repeating schedule, the increment level, the voltage threshold, or the base amplitude level.

In one embodiment, the present disclosure provides an electrotherapy device comprising a first enclosure enclosing (i) an electric signal generator configured to generate an electric signal, and (ii) a controller configured to control the generation of the electric signal, a first electrode in electric communication with the signal generator, a first connector in electric communication with the signal generator, a second enclosure enclosing (1) a battery holder comprising a positive contact and a negative contact configured to be able to hold a battery, (2) a charging and protection circuit configured to prevent overdrain and overcharge of the battery, and (3) a battery indicator configured to indicate a status of the battery, a second electrode in electric communication with the charging and protection circuit, and a second connector in electric communication with the charging and protection circuit, wherein the first connector and the second connector are detachably connected to enable electric communication between the signal generator and the charging and protection circuit, and wherein the first electrode and the second electrode have a maximum distance of at least 25 cm.

In some aspects, the first electrode is disposed on a surface of the first enclosure and has a shape suitable for application on a skin of a human subject.

In some aspects, the second electrode is disposed on a surface of the second enclosure and has a shape suitable for application on a skin of a human subject.

In some aspects, the device further comprises a first electric wire connecting the first enclosure and the first connector. In some aspects, the device further comprises a second electric wire connecting the second enclosure and the second connector. In some aspects, the combined length of the first wire and the second wire is at least 20 cm.

In some aspects, the device further comprises a battery placed in the battery holder.

In some aspects, the indicator is a light.

In some aspects, the first electrode and the second electrode have a maximum distance of at least 250 cm.

BRIEF DESCRIPTION OF THE DRAWINGS

Provided as embodiments of this disclosure are drawings which illustrate by exemplification only, and not limitation, wherein.

It will be recognized that some or all of the figures are schematic representations for exemplification and, hence, that they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Battery-driven stimulators for electrotherapy usually equip with a small battery to generate specified current waveforms applied to human body for stimulation. Such current waveforms can easily get into a saturated status due to high bio-impedance and low battery power. The present disclosure provides systems and methods that overcome this problem. In one embodiment, the waveform is adjusted according to feedbacks taken from a patient to reduce or avoid saturation. In another embodiment, the system includes a detachable battery pack that enables convenient use and charging of a battery in the battery pack.

Progressive Waveform Adjustment

For a battery that has a preset working voltage range, the current of its output waveforms is restricted by bio-impedance that usually is high, such as 200 KOhm or above, at an early stage, and gradually comes down to an acceptable level, 2 KOhm or less, after minutes or hours. This bio-impedance is carried by electrodes that apply stimulation signals to human body to gradually establish ionic channels to reduce bio-impedance.

A conventional electrotherapy device typically does not take the influence of the bio-impedance into consideration, but simply generates a predetermined waveform that can result in a saturated output waveform (i.e., exceeding working power range), or an invalid output waveform for electrotherapy.

It is herein discovered that progressive adjustment of a current waveform can be used to reduce or even prevent occurrence of saturated waveform outputs. The adjustment can take the voltage between the electrodes as input when the electrodes are applied on the skin or body of a human patient. The voltage can be directly measured or derived from other parameters, as further described below.

One objective of the adjustment is to gradually increase the voltage within a suitable range at an appropriate pace. For instance, if the determined voltage is below the upper limit of the range, the system then increases the amplitude of the waveform output by a certain interval. The voltage determination can be repeated at a desired frequency, until the voltage reaches or exceeds the upper limit, at which point the amplitude is reduced to a base level. Afterwards, the voltage determination can continue; so will the increase of the amplitude after each determination.

Figure 1:
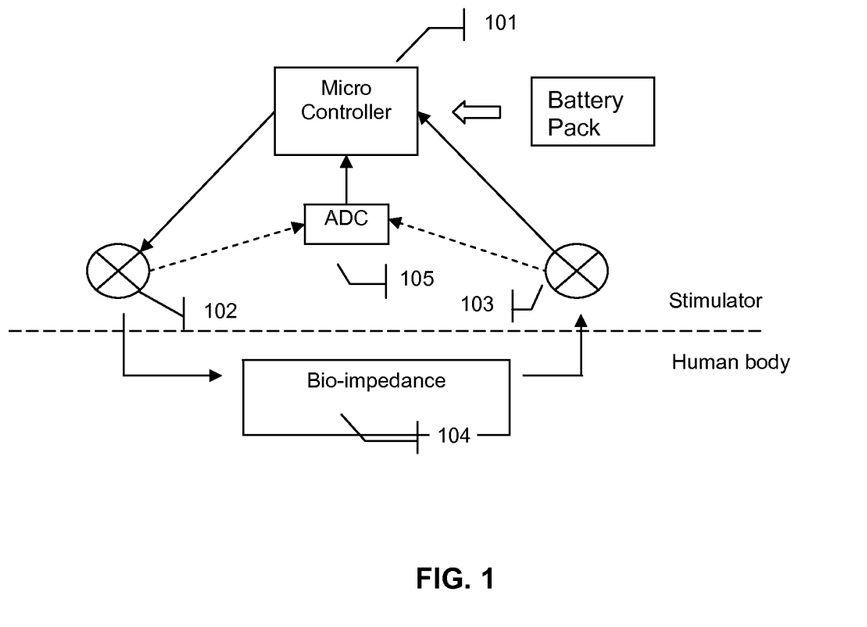
FIG. 1 illustrates an electrical circuit suitable for implementing one embodiment of the progressive adjustment of the disclosure.

FIG. 1 illustrates an electrical circuit suitable for implementing such progressive adjustment. The micro controller 101 includes at least a waveform generator such as a pulse wave generator (e.g., a square wave generator), a processor, and memory that embeds program code for carrying out desired control of the waveform generator. The micro controller is connected to two electrodes 102 and 103 that output generated current waveforms to bio impedance 104 (e.g., in a patient body). The current waveform path, as shown, starts from 101, 102, 104 to 103, and back to 101. The analog-to-digital convertor (ADC) 105 can take instruction from the micro controller 101 to gather voltage potentials from electrodes 102 and 103.

Figure 2:
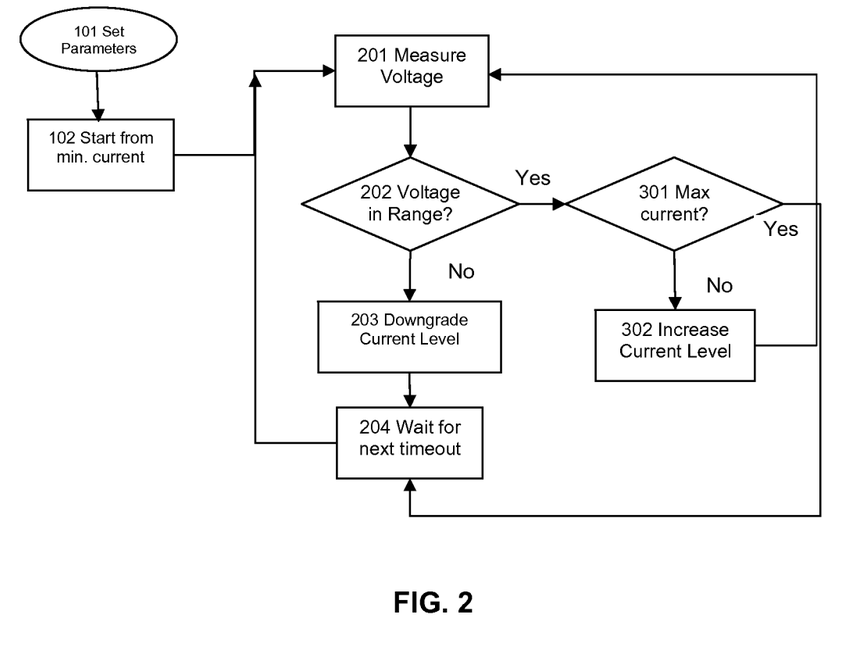
FIG. 2 is an example flowchart illustrating the adjustment of the waveform output for optimized electrotherapy.

FIG. 2 is an example flowchart illustrating the adjustment of the waveform output for optimized electrotherapy.

A. Initialization

Step 101 initializes the process at which point the following parameters can be set: (a) voltage determination schedule (e.g., a constant time interval), (b) voltage upper limit, (c) maximum and minimum amplitudes, and (d) amplitude increase interval.

The voltage determination schedule, in one aspect, can be a fixed schedule such as repeating the determination at a constant time interval. In another aspect, the interval can increase or decrease where needed. In yet another aspect, the schedule includes a rule for setting the schedule on the fly. For instance, the schedule can be adjusted depending on the determined voltage. For example, when the voltage is close to the upper limit, the determination can be carried out more frequently.

The voltage upper limit can be a fixed value, or set with a user profile, user preference, user input or by the system. Likewise, the maximum and minimum amplitudes for the waveform output can initialized. The amplitude increase interval can be a constant number or determined according to the voltage upper limit, and/or the maximum and minimum amplitudes.

The amplitude of the waveform can have a range from 1 µA to 100 mA, in some aspects. Alternatively, the minimum amplitude can be 2 µA, 3 µA, 4 µA, 5 µA, 10 µA, 20 µA, 30 µA, 50 µA or 100 µA. In some aspects, the maximum amplitude can be 100 µA, 150 µA, 200 µA, 250 µA, 300 µA, 400 µA, 500 µA, 1 mA, 5 mA, 10 mA, 20 mA, 50 mA, 60 mA or 100 mA.

In some aspects, the waveform has a frequency from 0.1 Hz to 200 Hz. In one aspect, the frequency is at least 0.1 Hz, or at least 0.2 Hz, 0.5 Hz, 1 Hz, 5 Hz, 10 Hz or 20 Hz. In one aspect, the frequency is not higher than 500 Hz, 400 Hz, 300 Hz, 200 Hz, 100 Hz, or 50 Hz.

In some aspects, the time interval is at least 5 seconds, or at least 10, 20, 30, 40, 50, or 60 seconds. In some aspects, the time interval is not longer than 30 seconds, or not longer than 60 seconds, 2 minutes, 3 minutes, 4 minutes, 5 minutes or 10 minutes.

In some aspects, the amplitude increase interval is at least 1 µA, or alternatively at least 2 µA, 3 µA, 4 µA, 5 µA, 10 µA, 20 µA, 50 µA, or 100 µA. In some aspects, the amplitude increase interval is not greater than 100 µA, 150 µA, 200 µA, 250 µA, 300 µA, 400 µA, 500 µA, 1 mA, 5 mA, or 10 mA.

In some aspects, the voltage upper limit is at least 1000 mV, 2000 mV, 3000 mV, 4000 mV, 5000 mV. In some aspects, the voltage upper limit is not higher than 5000 mV, 7000 mV, 9000 mV, 10,000 mV, 12,000 mV or 15,000.

At step 102, the waveform generator generates a current waveform with the minimum amplitude.

B. Voltage Determination

At step 201, the voltage between the electrodes can be determined by ADC sampling, which represents a product of current waveform and bio-impedance. Alternatively, the voltage can be computed from the amplitude and ADC sampling of the bio-impedance.

C. Adjustment

At step 202, the determined voltage is compared to the voltage upper limit. If the voltage is close to, equal to, or over the upper limit, then the system adjusts the waveform generation to decrease its output's amplitude (step 203). In one aspect, the amplitude is decreased to a base amplitude level (e.g., the minimum amplitude set at step 101).

If the voltage is lower than the upper limit, then the system adjusts the waveform generation to increase its output's amplitude (step 302) by the increase interval set at step 101. In some aspects, a step 301 is included to ensure that the amplitude does not exceed the maximum amplitude allowed by the system. Due to unpredictable changes of bio-impedance from electrodes, continuous monitoring of the current waveform is preferred to ensure that voltage is in a desired working range. In either scenario, the system will continue to monitor the voltage (step 204).

The voltage upper limit, in some aspects, can be dynamically changed. For instance, at step 202, the microcontroller can measure the battery voltage range from the battery pack. Then, the measured battery voltage range can be used to adjust the voltage upper limit. For instance, if the measured battery voltage range has shifted downwards, then the voltage upper limit can be reduced too, by, e.g., 0.05, 0.1 or 0.2 volt, or by certain percentage (e.g., 1%, 2%, 5%, 10%).

Battery Pack

Another embodiment of the present disclosure provides an electrotherapy device that includes a battery pack which is detachably connected to a stimulation pack that includes a waveform generator and control circuits. Without limitation, the stimulation pack can include a microprocessor, digital and analog circuits such as waveform generator, memory, IO pin, oscillator, and/or ADC and DAC.

Figure 3A:
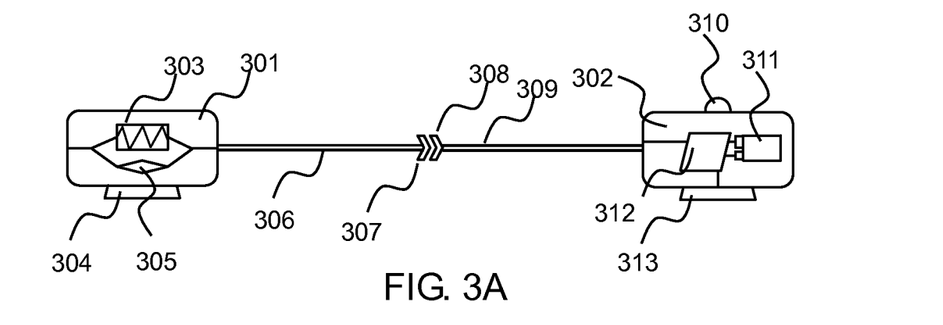
FIG. 3A-C show three example configurations of battery pack, stimulation pack, connecting wire and connectors and electrodes.

With reference to FIG. 3A, in one embodiment, the electrotherapy device includes two detachably connected packs (or enclosures), a battery pack 302 and a stimulation pack 301. The stimulation pack contains at least an electric signal (waveform) generator 303 configured to generate an electric signal and a controller 305 configured to control the generation of the electric signal. The stimulation pack can be connected to a first electrode 304 and to a first connector 307 each of which is in electric communication with the signal generator 303.

The battery pack can contain at least a battery holder 311 for holding a battery, which holder includes a positive contact and a negative contact. The battery pack, in one aspect, further includes a charging and protection circuit 312 configured to prevent overdrain and overcharge of the battery and a battery indicator 310 configured to indicate a status of the battery. Like the stimulation pack, the battery pack can also be connected to a second electrode 313 and to a second connector 308 each in electric communication with the battery or the charging and protection circuit 312. In some embodiments, the device further includes a battery, such as a rechargeable battery, in the battery holder.

The first connector 307 and the second connector 308 can be detachably connected to enable electric communication between the signal generator 303 and the charging and protection circuit 312. Further, the first electrode and the second electrode have a maximum distance of at least 25 cm (or 30 cm, 40 cm, 50 cm, 100 cm, 200 cm, 250 cm, or 300 cm) such that they can be placed on different locations of the body of a patient.

In some aspects, each of the packs can be connected to the corresponding connector through an electric wire (e.g., 306 and 309). In one aspect, one of the connectors can be directly disposed on the pack. For instance, in FIG. 3B, connector 308 is connected to the battery pack directly, whereas the stimulation pack is connected to connector 307 through a wire 314.

Figure 3B:
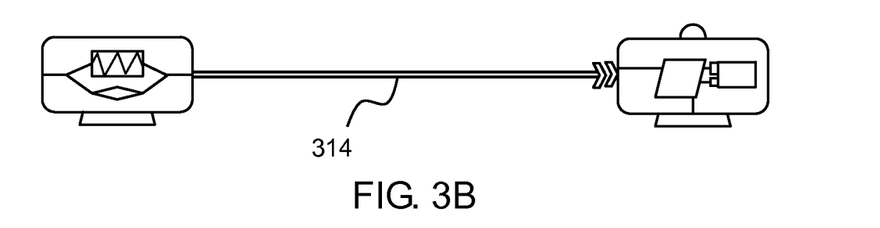
Figure 3C:
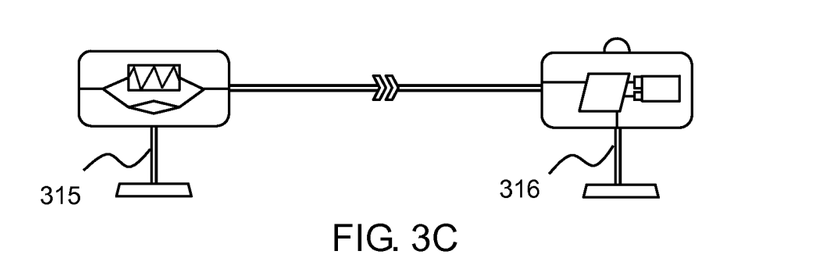

In some aspects, the electrodes are attached to the packs directly, as shown in FIG. 3A-B. In some aspects, the electrodes can be connected to the packs through a wire, such as wires 315 and 316 in FIG. 3C.

Figure 4:
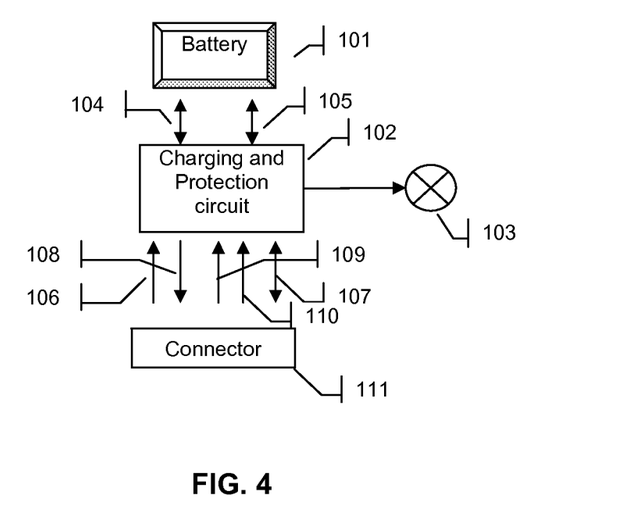
FIG. 4 shows one embodiment of the battery pack which includes a battery, a protection circuit, an indicator and a connector.

FIG. 4 shows one embodiment of the battery pack which includes a battery, a protection circuit, an indicator and a connector. Charging and Protection Circuit 102 is a charging chip-based circuit that monitors and controls over-charging when charging battery and overdrain when supplying power to stimulation pack.

Still in FIG. 4, indicator 103 is controlled by Charging and Protection Circuit 102 to indicate status, e.g., with a variety of lighting form, such as red blinking for in charging, green for charging complete or battery working normal, red for battery low or over temperature warning, or green blinking for other status.

VDD 104 and Ground 105 are bi-directional signals. When in charging, these two signals are input to Battery 101. When in supplying, they are output from Battery 101.

Figure 5:
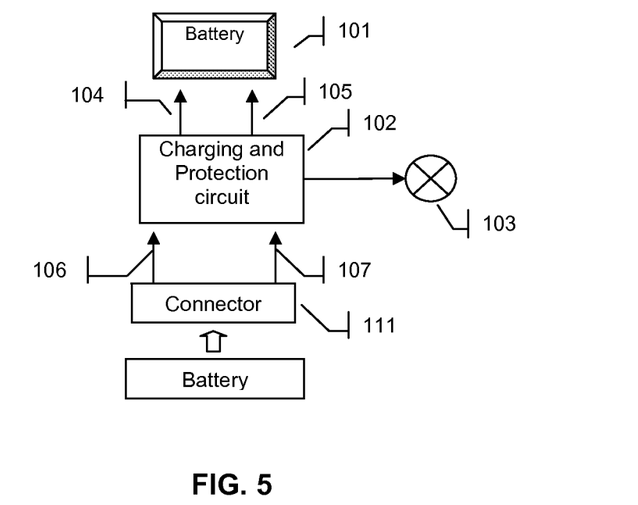
FIG. 5 shows one embodiment of the battery pack that is connected to another batter (or a power source) for charging.

VDD-In 106, GND 107, VDD-Out 108, Status 109 and Signal 110 constitute an interface to support charging, supplying, and other usages (FIG. 5). Those input and output signals as illustrated can be assigned to a Connector 111 compliance with some standard interface such as Micro USB that is reusable and could serve for multi-purposes.

For charging the battery (charging mode), VDD-In 106 and GND 107 can connect to a battery charger via Connector 111. Protection Circuit 102 will monitor the status such as overcharging or charging complete, route and signal to Battery 101, and lit the Indicator 103 for status. The Battery unit can be charged by multiple sources such as standard charger, computer and external battery pack etc.

When the battery is used to supply energy (supplying mode, see FIG. 6) to the stimulation pack, the battery pack can connect to the stimulation pack using the same interface (connector).

Figure 6:
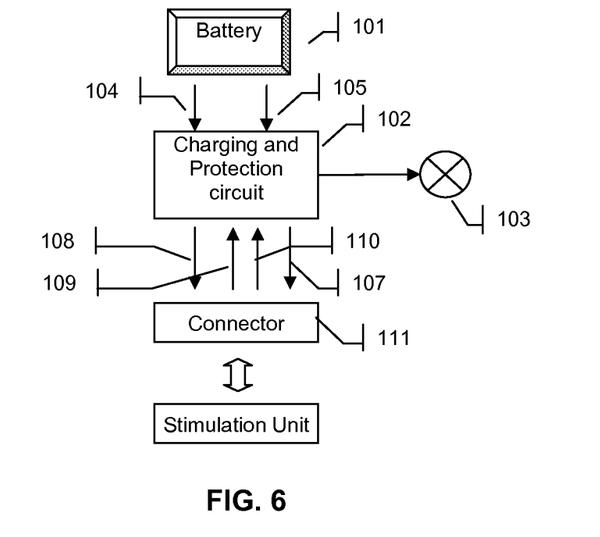
FIG. 6 shows one embodiment of the battery pack that is connected to a stimulation pack.

The Protection Circuit 102 can determine if the battery should be in supplying mode, and assign VDD-Out 108 and GND 107 for power output. Also, the Protection Circuit can prevent battery from battery overdrain. Indicator 103 can be controlled by Status 110 to share with the stimulation unit for status presentation.

Figure 7:
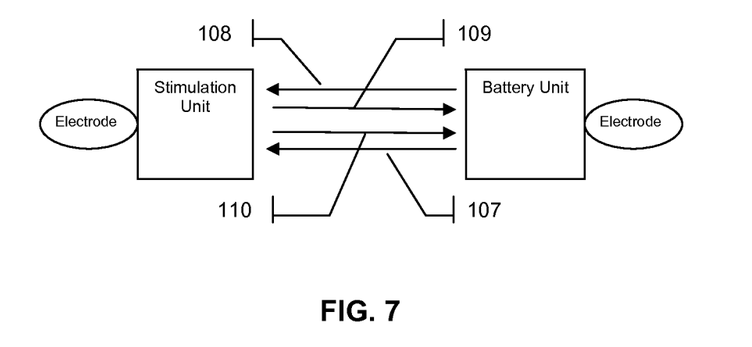
FIG. 7 illustrates electrical connection between a battery pack and a stimulation pack.

When connected to the stimulation pack, the battery pack supplies power signal 108 and 107 to the stimulation pack, and take input Status 109 signal to drive Indicator of Battery unit, and Signal 110 to drive the electrodes (FIG. 7).

When disconnected, the connector of the battery pack can be used for charging the battery by connected to a power source. Such an arrangement can eliminate the risk of electric shock to human body as charging won't be able to be performed unless the battery pack is disconnected from the stimulation pack.

In some instances, the two electrodes can be placed in distant positions, such as one on a foot and the other on a shoulder, for electrotherapy, one or more cable such as MicroUSB cable could be plugged in between the connector of battery pack and the connector of the stimulation unit for longer range of placement.

It is noted that the connector can also be used as a switch to cut off power supplying, instead of an extra switch on either the stimulation pack or the battery pack, so as to reduce the size and cost.

Use of the Battery Pack to Generate Biphasic Waveforms

The battery packs of the present disclosure are suitable for generating biphasic waveforms that are useful for obtaining further more complicated waveforms useful for micro current therapies. A non-limiting system and method for generating biphasic waveform is described in U.S. patent application Ser. No. 14/823,978, entitled "Systems and Methods for Generating Biphasic Waveforms," filed Aug. 11, 2015, which claims benefit under 35 U.S.C. § 119(e) of U.S. Provisional Application 62/084,202, filed Nov. 25, 2014. The content of each of these applications is incorporated to the present disclosure by reference in its entirety.

In some embodiments, the progressive adjustment of the waveforms can be applied to the biphasic waveforms, thus increasing the efficiency of these waveforms.

The biphasic system uses a constant current source and/or a constant current sink with one power source to generate biphasic waveforms. In one example, a positive, constant current is generated from a single constant current source, and then applied to either end of an output workload in an alternating manner, such as at a predefined frequency.

In another example, a constant current source is used to generate a positive phase, and a constant current sink is used to generate a negative phase. An alternating adoption of these two phases, therefore, gives rise to the application of a biphasic waveform on an output workload.

One embodiment of the biphasic system is a system for generating a biphasic waveform to a workload, comprising: a constant current source configured to generate a constant current; a first switch having a first end and a second end, wherein the first end switches between the current source and the ground; a second switch having a third end and a fourth end, wherein the third end switches between the current source and the ground; and a microcontroller configured to set the first switch and the second switch to alternate between configurations (a) and (b): (a) the first end connects to the current source and the third end connects to the ground; and (b) the first end connects to the ground and the third end connects to the current source, wherein, when a workload is connected to the second end of the first switch and the fourth end of the second switch, configuration (a) allows the constant current to be applied to the workload from the first switch, through the workload and the second switch, to the ground, and configuration (b) allows the constant current to be applied to the workload from the second switch, through the workload and the first switch, to the ground, thereby applying a biphasic waveform with alternating phases to the workload.

Another embodiment of the biphasic system is a system for generating a biphasic waveform to a workload, comprising: a constant current source configured to generate a constant first current; a current sink; a switch having a first end and a second end, wherein the second end switches between a power supply and the ground; and a microcontroller configured to set the current source, the current sink, and the switch to alternate between configurations (a) and (b): (a) the current sink is deactivated or disconnected and the switch connects to the ground; and (b) the current source is deactivated or disconnected and the switch connects to the power supply, wherein, when a workload is connected to the second end of the switch and the current source or the current sink, configuration (a) allows the constant first current to be applied to the workload from the current source, through the workload and the switch, to the ground, and configuration (b) allows the current sink to absorb a second current from the power supply, through the switch and the workload, thereby applying a biphasic waveform with alternating phases to the workload.

A "biphasic waveform" is a current waveform that includes primarily two phases appearing in an alternating manner. In one aspect, one of the phases is positive and the other negative. In another aspect, both phases are positive or negative, but one has a higher amplitude than the other. In one aspect, both phases are constant or substantially constant. In another aspect, the phases are asymmetric such as one with a positive of square wave and a negative in sine wave. In another aspect, the phases are symmetric such as sine waves.

In a particular embodiment, the biphasic waveform comprises a constant positive phase and a constant negative phase having the same or substantially the same amplitudes. Nevertheless, it is readily appreciated that the devices and methods of the present disclosure can be used to generate any biphasic waveforms, including symmetric and asymmetric waveforms.

In one embodiment, the biphasic system includes a microcontroller, a current source, two control switches, and optionally a convertor. In some instances, the current source is a constant current source, generating positive, constant current.

A "current source" is an electronic circuit that delivers an electric current which is independent of the voltage across it. A current source can be an independent current source that delivers a constant current. A dependent current source, by contrast, delivers a current which is proportional to some other voltage or current in the circuit.

Current sources are different from voltage sources. A theoretical voltage source would have a zero ohm output impedance in series with the source. A real-world voltage source has a very low, but non-zero output impedance: often much less than 1 ohm. By contrast, a current source provides a constant current, as long as the load connected to the source terminals has sufficiently low impedance. An ideal current source would provide no energy to a short circuit and approach infinite energy and voltage as the load resistance approaches infinity (an open circuit). An ideal current source has an infinite output impedance in parallel with the source. A real-world current source has a very high, but finite output impedance.

The microcontroller can control the operation of a constant current source, such as sending a digital waveform to the constant current source or turn it on or off. Further, the microcontroller regulates the control switches, optionally through a controlling convertor that converts digital control signal from the microcontroller to the control pins of two switches (first and second switches).

The two switches, for instance, can be multiplexer (or mux) type switches. Each switch can include a control pin that is controlled by the microcontroller. The first has two terminals, one connected to an output workload when in use, and the other switching between the output terminal of the current source and the ground. Likewise, the second switch has two terminals, one connected to an output workload when in use (the opposite side from the terminal of the first switch), and the other switching between the output terminal of the current source and the ground.

When in operation, the device is connected to an output workload, through two terminals of both switches. The microcontroller controls both switches to set in two different configurations in an alternating manner.

In configuration (a), the first switch connects with the current source and the second switch connects to the ground. Therefore, in this configuration, the current from the current source goes through the first switch, the workload, the second switch, and to the ground.

In configuration (b), the first switch connects to the ground and the second switch connects with the current source. Therefore, in this configuration, the current from the current source goes through the second switch, the workload, the first switch, and to the ground.

When the microcontroller controls the switches to alternate between configurations (a) and (b), therefore, the workload receives the current from two opposite directions, resulting in an application of a biphasic waveform on the workload.

In another embodiment, the biphasic system includes a microcontroller, a current source, a control switch, a positive supply voltage (VDD), and a current sink. In some instances, the current source is a constant current source, generating positive, constant current. In some instances, the current sink is a constant current sink, that generates a constant current by absorbing currents from the VDD.

The microcontroller can control the operation of the current source and the current sink. Further, the microcontroller regulates the switch.

The switch, for instance, can be multiplexer (or mux) type switches. The switch can include a control pin that is controlled by the microcontroller. The switch has two terminals, one connected to an output workload when in use, and the other switching between the ground and the VDD.

When in operation, the device is connected to an output workload which, at one end, connects to the current source and the current sink, and at the other end, connects to the switch. Accordingly, the microcontroller can control the switch to set in two different configurations in an alternating manner.

In configuration (a), the switch connects with the ground. Optionally, at this configuration, the microcontroller turns off the current sink and/or voltage supply VDD. Therefore, in this configuration, the current from the current source goes through the workload and the switch, and to the ground.

In configuration (b), the switch connects to the voltage supply VDD. Optionally, at this configuration, the microcontroller turns off the current source. Therefore, in this configuration, a current arises from VDD, going through the workload into the current sink.

When the microcontroller controls the switch to alternate between configurations (a) and (b), therefore, the workload either receives a current from the current source or from the voltage source absorbed by the current sink. These currents come from two opposite directions, resulting in an application of a biphasic waveform on the workload.

The amplitudes of the currents generated by the current sources can be adjusted as needed. For instance, for therapeutic use, the amplitude can in general be from 1 μA to 200 μA, or alternatively from 5 μA to 100 μA, from 20 μA to 80 μA, from 30 μA to 60 μA or from 30 μA to 50 μA.

The frequency of the biphasic waveform can also be adjusted depending on needs. For instance, the frequency (i.e., the alternating frequency) can be from 0.1 Hz to 200 Hz. In some aspects, the frequency is greater than 0.1 Hz, 0.2 Hz, 0.5 Hz, 1 Hz, 2 Hz, 5 Hz, 10 Hz or 20 Hz. In some aspects, the frequency is lower than 200 Hz, 180 Hz, 150 Hz, 100 Hz, 90 Hz, 80 Hz, 70 Hz, 60 Hz, 50 Hz, 40 Hz, 30 Hz, 20 Hz, 10 Hz or 5 Hz.

The waveforms of the present disclosure can be used to generate voltage potentials suitable for stimulating excitable cells in a human body so that the cell enters a polarization stage. To trigger a cell like a nerve cell to enter such stage, a voltage potential change has to be large enough to reach a threshold (usually between −20 mV and −65 mV depending on type of cell or nerve).

Use of the Battery Pack to Generate Overshoot Waveforms

The battery packs of the present disclosure are also suitable for generating other waveforms, such as base waveforms with overshoot signals useful for micro current therapies. A non-limiting system and method for generating and using overshoot waveforms is described in U.S. patent application Ser. No. 14/823,992, entitled "Overshoot Waveform in Micro Current Therapy," filed Aug. 11, 2015, which claims benefit under 35 U.S.C. § 119(e) of U.S. Provisional Application 62/037,029, filed Aug. 13, 2014. The content of each of these applications is incorporated to the present disclosure by reference in its entirety.

In some embodiments, the progressive adjustment of the waveforms can be applied to the overshoot waveforms or the base pulse forms of the overshoot signals, thus increasing the efficiency of these waveforms.

Square waveforms that generate constant current are generally operated in low voltage amplitudes and are discovered to be less effective in exciting cells or nerves. Although the voltage and frequency can be adjusted to improve stimulation, such adjustment may offset the therapeutic benefits.

An improved waveform includes overshoot signals overlaid on constant currents and is capable of stimulating cells or nerves to achieve healing. In one embodiment, the system includes an oscillator configured to generate a reference signal, a pulse wave generator to generate a pulse waveform signal based on the reference signal, an overshoot generator to generate an overshoot signal based on the reference signal, and an output module to generate a composite output waveform signal based on the overshoot signal and the pulse waveform signal, wherein the composite output waveform includes one or more pulses having one or more overshoots that extend a width of each of the pulses. The system can be adjusted by a user depending on the disease, condition, or preference of the user.

A square waveform (or more generally a pulse waveform) can incorporate overshoot signals that improve the ability to stimulate cells to achieve therapeutic benefits. The base pulse waveform can be conventional pulse waveform and can be mono-phasic or biphasic. Each phase can be substantially constant, that is, the variation (e.g., the standard deviation of the amplitude within each phase) is within 10% (or 5%) of the amplitude.

The amplitude of the base pulse waveform can be adjusted, and is in general from 1 μA to 200 μA, or alternatively from 5 μA to 100 μA, from 20 μA to 80 μA, from 30 μA to 60 μA or from 30 μA to 50 μA. In one aspect, the overshoot signal has a rapid rising phase that could go over threshold potential for cell or nerve polarization. The overshoot signal can have a slow falling phase and resting phase of overshoot signal and decay into base pulse wave stage. Overshoot signal can occur multiple times (e.g., at least 2, at least 3, at least 4, at least 5 times) in a single phase with a frequency resonating with the type of cell and nerve.

The frequency of the base pulse wave can also be adjusted, for instance, by a user through an input module. In general, the frequency is from 0.1 Hz to 200 Hz. In some aspects, the frequency is greater than 0.1 Hz, 0.2 Hz, 0.5 Hz, 1 Hz, 2 Hz, 5 Hz, 10 Hz or 20 Hz. In some aspects, the frequency is lower than 200 Hz, 180 Hz, 150 Hz, 100 Hz, 90 Hz, 80 Hz, 70 Hz, 60 Hz, 50 Hz, 40 Hz, 30 Hz, 20 Hz, 10 Hz or 5 Hz.

The base pulse wave can be bisphasic or mono-phasic waveforms. In some aspects, the base pulse wave is a square wave.

The overshoot waveforms can be used to generate voltage potentials suitable for stimulating excitable cells in a human body so that the cell enters a polarization stage. To trigger a cell like a nerve cell to enter such stage, a voltage potential change has to be large enough to reach a threshold (usually between −20 mV and −65 mV depending on type of cell or nerve).

An overshoot signal that is suitable for generating a composite outcome waveform can have a rising edge (left of the peak) that is steeper than a falling edge (right of the peak). The rising edge, in some aspects, reaches the peak within 2 ms, or alternatively within 0.1 ms, 0.2 ms, 0.3 ms, 0.4 ms, 0.5 ms, 0.6 ms, 0.7 ms, 0.8 ms, 0.9 ms, 1 ms, 1.2 ms, 1.5 ms, or 1.8 ms.

In some aspects, the failing edge shows a plateau, which can last from 0.5 ms to 10 ms. In some aspects, the time span of the falling edge (from peak to back to a pulse phase) is at least twice (or alternatively 3×, 4×, 5×, 10×) the time span of the rising edge (from a pulse phase to peak). The gradual falling of the overshoot amplitudes helps to achieve the resting state of polarization and avoid another threshold triggering before the previous polarization stage is completed.

In some aspects, there is a resting period between each overshoot signal. In one aspect, the resting period is at least 0.5 ms, or alternatively at least 1 ms, 1.5 ms, 2 ms, 3 ms, 4 ms or 5 ms. In one aspect, the resting period is not longer than 20 ms, 10 ms, 5 ms, 4 ms, 3 ms or 2 ms. In one aspect, the resting period is at least 50% of the time span of the overshoot signal, or alternatively at least 75%, 100%, 150%, 2×, 3×, 4× or 5× of the time span of the overshoot signal. In one aspect, the resting period is not longer than 2×, 3×, 4×, 5×, 10× or 20× of the time span of the overshoot signal.

The frequency, shape and amplitude of the overshoot signals can be adjusted. The peak amplitude, in general, is adequate to genera a 0 to +/−100 mV voltage potential, and in some aspects between −20 mV and −65 mV depending on type of cell or nerve. In some aspects, the amplitude of the overshoot signal is between 1 μA and 600 μA. In one aspect, the amplitude of the overshoot signal is greater than 1 μA, 2 μA, 3 μA, 4 μA, 5 μA, or 10 μA. In one aspect, the amplitude of the overshoot signal is less than 500 μA, 400 μA, 300 μA, 200 μA, 100 μA, 90 μA, 80 μA, 70 μA, 60 μA, 50 μA, 40 μA, 30 μA, 20 μA, or 10 μA. In some aspects, the amplitude of the overshoot signal is at least 10%, or alternatively at least 20%, 30%, 40%, 50%, 75%, 100%, 150%, 200% or 250% of the amplitude of the base pulse signal. In some aspects, the amplitude of the overshoot signal is not greater than 10 times, 9 times, 8 times, 7 times, 6 times, 5 times, 4 times, 3 times, or twice of the amplitude of the base pulse signal.

The frequency of the overshoot signals can be greater than that of the base pulse waveform, so that each phase of the base pulse waveform is superimposed (or overlaid) with at least an overshoot signal. In one aspect, the frequency is at least 1 Hz, or alternatively at least 2 Hz, 5 Hz, 10 Hz, 15 Hz, 20 Hz, 30 Hz, 40 Hz, 50 Hz, 100 Hz, 150 Hz or 200 Hz. In some aspects, the frequency is not greater than 5 KHz, 2 KHz, 1 KHz, 500 Hz, 200 Hz, 150 Hz or 100 Hz.

In some aspects, the frequency, amplitude, shape, resting period, of any of the above waveforms or signals can be adjusted on the fly during a therapy. The adjustment can be automatic or triggered by input from a user.

An example system useful for generating an overshoot waveform is also provided, which can include an Overshoot Generator that represents a micro-controller based component that is programmable to produce digitized overshoot signal according to requested parameters, and output digitized overshoot. Also included is a Pulse Wave Generator that is a programmable component that takes requested parameters to generate digitized pulse wave signal. Both the Overshoot Generator and the Pulse Wave Generator are connected to an Oscillator for signal synchronization. Both digitized signals can be sent to a composition component for composition, and sent to digital-to-analog converter (DAC)/Shifting to convert into analog signal.

An oscillator herein is an electronic circuit that synchronizes the generation of pulse waves and overshoot waves in a digital format. A digital-to-analog converter (DAC) is a function that converts digital data (usually binary) into an analog signal (current, voltage, or electric charge). An analog-to-digital converter (ADC) performs the reverse function.

In some aspects, the system further includes wires and/or electrodes to connect to the skin or other organs of a human subject so as to apply an output waveform to the user. in some aspects, the system further includes an input module or device that takes an input from the user. The input can then be used to start, stop or adjust the waveform applied to the user. In one aspect, the input module is wired to the system and in another aspect, the input module communicates with the system wirelessly. In some aspects, the input module includes a graphic user interface. In some aspects, the system includes a processor to take the input and implement adjustments.

Methods of micro current electrotherapy are also provided, in some embodiments. The output waveforms that can be generated from the systems are applied to a human subject. Various parameters of the waveforms can be adjusted to suit the user or the particular disease or condition that the user has, such as back pain, arthritis at the knee, or wound on the skin.

A micro current electrotherapy entails sending relatively weak electrical signals into the body of an individual in need of the therapy. Such therapies apply small (e.g., between 1 and 50 microampere) electrical currents to nerves using electrodes placed on the skin. Micro current electrotherapies can be used in treatments for pain, age-related macular degeneration, wound healing, and tendon repair, without limitation. Many micro current treatments concentrate on pain and/or speeding healing and recovery. Micro current treatments are commonly used by professional and performance athletes with acute pain and/or muscle tenderness as they are drug-free and non-invasive, thus avoiding testing and recovery issues. They can also be used as a cosmetic treatment.

Therapy Methods

Methods of electrotherapy are also provided, in some embodiments. The output waveforms that can be generated from the systems are applied to a human subject. Various parameters of the waveforms can be adjusted to suit the user or the particular disease or condition that the user has, such as back pain, arthritis at the knee, or wound on the skin.

A micro current electrotherapy entails sending relatively weak electrical signals into the body of an individual in need of the therapy. Such therapies apply small (e.g., between 1 and 50 microampere) electrical currents to nerves using electrodes placed on the skin. Micro current electrotherapies can be used in treatments for pain, age-related macular degeneration, wound healing, and tendon repair, without limitation. Many micro current treatments concentrate on pain and/or speeding healing and recovery. Micro current treatments are commonly used by professional and performance athletes with acute pain and/or muscle tenderness as they are drug-free and non-invasive, thus avoiding testing and recovery issues. They can also be used as a cosmetic treatment.

Although the discussions above may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure. Such variations will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed here. For example, the terms "comprising", "including," containing," etc. shall be read expansively and without limitation. Additionally, the terms and expressions employed here have been used as terms of description and not of limitation; hence, the use of such terms and expressions does not evidence and intention to exclude any equivalents of the features shown and described or of portions thereof. Rather, it is recognized that various modifications are possible within the scope of the disclosure claimed.

By the same token, while the present disclosure has been specifically disclosed by preferred embodiments and optional features, the knowledgeable reader will apprehend modification, improvement and variation of the subject matter embodied here. These modifications, improvements and variations are considered within the scope of the disclosure.

The disclosure has been described broadly and generically here. Each of the narrower species and subgeneric groupings falling within the generic disclosure also form part of the disclosure. This includes the generic description of the disclosure with a proviso or negative limitation removing any subject matter from the genus, regardless of whether or not the excised material is described specifically.

Where features or aspects of the disclosure are described by reference to a Markush group, the disclosure also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the disclosure has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A micro current therapy device comprising:
    a pulse wave generator configured to generate a pulse waveform signal;
    a first electrode and a second electrode each in electric communication with the pulse wave generator;
    an analog-to-digital converter (ADC) in electric communication with the first electrode and the second electrode and configured to measure a voltage between the first electrode and the second electrode when the first electrode and the second electrode are connected to a conductive subject at two separate locations; and
    a controller comprising a processor, a memory and program code which, when executed by the processor, configures the controller to:
        (a) receive the voltage from the ADC as input at a predetermined schedule; and
        (b) increase the amplitude by a predetermined increase interval if the voltage is lower than a voltage upper limit, or lower the amplitude to a base amplitude level if the voltage is the same as or higher than voltage threshold.

2. The device of claim 1, wherein the schedule has a predetermined interval.

3. The device of claim 2, wherein the interval is from 10 seconds to 60 seconds.

4. The device of claim 1, wherein the voltage upper limit is from 3000 mV to 9000 mV.

5. The device of claim 1, wherein the base amplitude level is from 0.01 mA to 60 mA.

6. The device of claim 1, wherein the increase interval is from 0.005 mA to 2 mA.

7. The device of claim 1, wherein the pulse waveform has a frequency from 0.1 Hz to 200 Hz.

8. The device of claim 1, wherein the pulse waveform has an amplitude from 1 µA to 200 µA.

9. A method for improving healing of a human subject in need thereof, comprising connecting the first electrode and the second electrode of the device of claim 1 to two locations of the human subject to the subject and configuring the device to apply wave forms to the human subject, thereby improving healing of the human subject.

10. The method of claim 9, wherein the device further comprises a user interface allowing a user to adjust the repeating schedule, the increment level, the voltage threshold, or the base amplitude level.

* * * * *